United States Patent
Watson et al.

(10) Patent No.: US 10,881,357 B1
(45) Date of Patent: Jan. 5, 2021

(54) SYSTEMS AND METHODS FOR MONITORING THE HEALTH OF VEHICLE PASSENGERS USING CAMERA IMAGES

(71) Applicant: Panasonic Avionics Corporation, Lake Forest, CA (US)

(72) Inventors: Philip Watson, Lake Forest, CA (US); Steven Bates, Mission Viejo, CA (US)

(73) Assignee: PANASONIC AVIONICS CORPORATION, Lake Forest, CA (US)

( * ) Notice: Subject to any disclaimer, the term of this patent is extended or adjusted under 35 U.S.C. 154(b) by 0 days.

(21) Appl. No.: 16/574,960

(22) Filed: Sep. 18, 2019

(51) Int. Cl.
| | |
|---|---|
| *A61B 5/00* | (2006.01) |
| *G06K 9/00* | (2006.01) |
| *G16H 30/40* | (2018.01) |
| *G16H 40/67* | (2018.01) |
| *B64D 11/00* | (2006.01) |
| *B64D 47/08* | (2006.01) |

(Continued)

(52) U.S. Cl.
CPC ............ *A61B 5/746* (2013.01); *A61B 5/0022* (2013.01); *A61B 5/02055* (2013.01); *A61B 5/165* (2013.01); *A61B 5/4809* (2013.01); *B64D 11/00151* (2014.12); *B64D 47/08* (2013.01); *G06K 9/00832* (2013.01); *G16H 30/40* (2018.01); *G16H 40/67* (2018.01); *H04N 7/18* (2013.01); *A61B 5/021* (2013.01); *A61B 5/024* (2013.01); *A61B 5/0816* (2013.01); *B60R 11/0217* (2013.01); *B60R 11/0235* (2013.01); *B60R 11/0247* (2013.01); *B60R 11/04* (2013.01); *B60R 2011/0012* (2013.01)

(58) Field of Classification Search
None
See application file for complete search history.

(56) References Cited

U.S. PATENT DOCUMENTS

| | | | |
|---|---|---|---|
| 2005/0080533 A1 | 4/2005 | Otman | |
| 2005/0090978 A1* | 4/2005 | Bathory | ............... G08G 5/0082 |
| | | | 701/469 |

(Continued)

FOREIGN PATENT DOCUMENTS

| | | |
|---|---|---|
| CN | 106687026 A | 5/2017 |
| JP | 2017029219 | 2/2017 |

*Primary Examiner* — Rebecca A Volentine
(74) *Attorney, Agent, or Firm* — Perkins Coie LLP

(57) ABSTRACT

Systems and methods for monitoring the health of vehicle passengers using images of the passengers taken by onboard imaging devices (e.g., digital cameras), determining health data (e.g., vital signs) on-board the passenger vehicle using the images, and communicating (in one or more instances) with a remote telemedical monitoring system to determine medical information regarding the passengers and/or enable communication with a medical caregiver for diagnosis and treatment. The system may be especially useful in larger passenger vehicles, such as commercial aircraft, to monitor the health of all or most of the passengers but may also be used in other passenger vehicles including passenger trains, buses, ships, boats and automobiles. In one or more instances, the systems and methods primarily utilize images to determine health data (e.g., vital signs) of the passengers, such that the health data is obtained without physically contacting the passengers (contactless), as opposed to typical vital sign devices which physically contact a person.

20 Claims, 9 Drawing Sheets

(51) Int. Cl.
*A61B 5/0205* (2006.01)
*A61B 5/16* (2006.01)
*H04N 7/18* (2006.01)
*A61B 5/021* (2006.01)
*B60R 11/02* (2006.01)
*B60R 11/00* (2006.01)
*B60R 11/04* (2006.01)
*A61B 5/024* (2006.01)
*A61B 5/08* (2006.01)

(56) References Cited

U.S. PATENT DOCUMENTS

| | | | |
|---|---|---|---|
| 2013/0009761 A1* | 1/2013 | Horseman | A61B 5/1114 340/425.5 |
| 2013/0338857 A1* | 12/2013 | Sampigethaya | G06F 19/3418 701/3 |
| 2017/0113801 A1 | 4/2017 | Brunaux et al. | |
| 2018/0068078 A1* | 3/2018 | Barthell | G06N 20/00 |
| 2018/0220939 A1 | 8/2018 | Matsuo et al. | |
| 2018/0310844 A1 | 11/2018 | Tezuka et al. | |
| 2019/0046120 A1 | 2/2019 | Sham | |
| 2019/0061772 A1* | 2/2019 | Prinz | A61B 5/747 |
| 2019/0133511 A1 | 5/2019 | Francesco | |
| 2019/0391581 A1* | 12/2019 | Vardaro | A61B 5/0205 |

\* cited by examiner

SYSTEMS AND METHODS FOR MONITORING THE HEALTH OF VEHICLE PASSENGERS USING CAMERA IMAGES

BACKGROUND

The field of the invention generally relates to monitoring the health status of passengers on passenger vehicles, such as airplanes, automobiles, trains, buses, etc., and more particularly, to systems and methods for monitoring the health of vehicle passengers using images of the passengers taken by onboard cameras, determining health data (e.g., vital signs), and communicating with a remote telemedical monitoring system to determine medical information regarding the passengers and/or enable communication with a medical caregiver for diagnosis and treatment.

There are various reasons it may be useful to monitor the health of passengers on a passenger vehicle, such as airplanes, trains, buses, and automobiles. For example, the health of passengers may be monitored to detect if a passenger has a health condition requiring attention, and if necessary, provide medical treatment. A common carrier (e.g., airline, train operator, bus operator, etc.) or agency may also monitor the health of passengers to detect passengers which may have a contagious disease and take action to prevent the spread of the disease, such as quarantining and/or treating such passengers. Monitoring the health of passengers can be used to diagnose a health condition, such as determining the severity of a passenger's condition to determine if urgent care is required. Furthermore, in some cases, a passenger may identify that they have a condition, such as being on oxygen, having a heart condition, or having high anxiety or panic from travel events (e.g., turbulence or fear of flying), and such passenger may wish to be monitored during travel so that crew members can respond timely and appropriately if the passenger experiences a situation requiring attention.

There is currently no system in operation to monitor the health of all passengers on a transport vehicle. Instead, existing methods of health monitoring of passengers are limited to individual devices which require physical contact with the passenger, such as electrodes, or other devices worn or attached to the passenger. In addition, the individual devices are not in communication with a centralized monitoring station on the transport vehicle.

A few methods and systems for monitoring the health of passengers on a vehicle have been previously disclosed. For instance, Japanese Published Patent Application No. JP 2017029219 A discloses a body temperature monitoring system for detecting in-flight passengers indicating a fever. The system utilizes a plurality of infra-red cameras mounted at positions around each seat to detect body temperature by radiant heat of each passenger. If a feverish patient is detected from the measured temperature data, a warning is displayed on a computer monitor installed in a flight attendant station identifying the seat location to notify the flight attendants. The system may also display a temperature history of the passenger, an entry-exit history, and/or other passenger information to allow the flight attendants to determine whether or not the feverish patient needs to be isolated.

Similarly, U.S. Published Patent Application No. 2017/0113801 A1 discloses a health monitoring system to be installed in a cabin of an aircraft or spacecraft having an imaging device, such as a visible light camera, a near-infrared lighting source combined with a near-infrared camera, a thermal camera and a range imaging device. The imaging device captures images of the passengers and analyzes the images to determine and indicate whether a passenger seat is occupied or empty. The application further describes that the captured images may be analyzed using content comparison between at least two images captured successively to detect movement or variation of the images in order to collect medical or health information about a passenger present at a particular passenger seat. The application states that the behavior observations may be useful in particular for identifying possible hijackers or nervous passengers, in order to trigger or implement appropriate actions.

It has also been previously disclosed to utilize image data to determine vital statistics of a human body. Utilizing images has the advantage of being a contactless means of obtaining vital statistics, including on multiple persons by simply aiming an imaging device (e.g., a camera) at each of the persons. For example, U.S. Published Patent Application No. 2018/0310844 A1 describes a method for stably estimating a pulse of a human body using time-sequential captured image data. A skin-color region is extracted from each of the captured images and a pulse estimator estimates a pulse based on the skin-color region. Similarly, U.S. Published Patent Application No. 2018/0220939 A1 discloses a method for using captured images of a human body to determine vital information, including an index indicating a living state of the human. The method entails capturing images, detecting a face region in the captured images, and extracting vital information from the captured images, including an index indicating a living state, and determining whether the face in the face region is in a living state, based on the vital information.

Still, there is a need for systems and methods for monitoring the health of vehicle passengers which can effectively and efficiently monitor the health of one or more passengers on a passenger vehicle and facilitate detection and diagnosis of health conditions and/or treatment by a medical caregiver.

SUMMARY

The present invention is directed to systems and methods for monitoring the health of vehicle passengers using images of the passengers taken by onboard imaging devices (e.g., digital cameras), determining health data (e.g., vital signs) using the images, and communicating with a remote telemedical monitoring system to determine medical information regarding the passengers and/or enable communication with a medical caregiver for diagnosis and treatment. The system may be especially useful in larger passenger vehicles, such as commercial aircraft, to monitor the health of all or most of the passengers but may also be used in other passenger vehicles including passenger trains, buses, ships, boats and automobiles. The systems and methods primarily utilize images to determine health data (e.g., vital signs) of the passengers, such that the health data is obtained without physically contacting the passengers (contactless), as opposed to typical vital sign devices which physically contact a person. For example, vital signs such as pulse rate, respiration rate, and body temperature are typically determined using conventional devices which contact the human body, such as a pulse rate monitor, respiration rate monitor (e.g., pulse oximeter, etc.), and thermometer.

In a first embodiment, a health monitoring system for monitoring health of passengers on a passenger vehicle includes an onboard management system installed on the vehicle, and an imaging device in communication with the onboard management system. The onboard management system includes a computing device having a computer processor, memory, a display monitor, system software, and a health monitoring software application. For instance, the onboard management system may include a computer similar to a personal computer. The health monitoring software application is a customized software application which programs the computing device to analyze images of a passenger to determine health data regarding the passenger, such as the passenger's vital signs. The health monitoring software application may utilize the methods as disclosed in U.S. Published Patent Application No. 2018/0310844 A1 and U.S. Published Patent Application No. 2018/0220939 A1, or any other suitable system or method to obtain health data of a person from images. All publications cited herein are incorporated by reference in their entireties, for all purposes.

The onboard management system also includes a vehicle communication module configured to communicate with a remote telemedical monitoring system via a communication network. For example, the vehicle communication module may be a cellular phone communication module (e.g., for ground vehicles, like trains, automobiles, and buses), a radio frequency air-to-ground communication module (e.g., for aircraft), a satellite communication module (e.g., for aircraft or ships), or the like, which can enable communication between the onboard management system and the remote telemedical monitoring system.

The remote telemedical monitoring system may be any suitable telehealth (also referred to as telemedicine) system which provides medical information via telecommunication. It typically allows a patient and a health caregiver (clinician) to have remote communication of health data, including vital information and symptoms of the patient, as well enabling the telemedical monitoring system to provide medical information. The medical information may include a health condition (i.e., a diagnosis), care, advice and/or treatment from the clinician. In another feature, the telemedical monitoring system may also be configured to provide automated medical information, such as health conditions, care, advice, and/or treatment based on the health data, with or without the assistance of a clinician. In another aspect, the telemedical monitoring system may also enable two-way, live communication between the clinician and the passenger or onboard caregiver via the onboard management system.

The health monitoring system also has an imaging device in communication with the onboard management system. The imaging device is configured to capture images of the passenger on the vehicle and transmit the images to the onboard computing system. For instance, the imaging device may be a digital camera which can capture either or both of still images and video images.

The health monitoring system is configured to perform the following process to monitor the health of the passengers on the vehicle. The imaging device captures images of the passenger. The imaging device transmits the images to the onboard management system. The onboard management system analyzes the images and determines health data regarding the passenger, such a vital signs, using the health monitoring application. The onboard management system transmits the health data to the telemedical monitoring system via the communication network. The telemedical monitoring system analyzes the health data and provides medical information, such as health condition, diagnosis, care, advice and/or treatment, to the onboard management system via the communication network. The onboard management system receives the medical information from the telemedical monitoring system based on the analysis of the health data by the remote telemedical system.

In another aspect of the health monitoring system, the passenger vehicle may be a common carrier vehicle having an onboard entertainment system (e.g., an in-flight entertainment system ("IFE") on an aircraft), and the imaging device may be a camera installed in each of the in-seat display systems, and/or other cameras installed throughout the vehicle (e.g., security cameras). In this way, the health monitoring system can monitor the health of all, or any selected ones, of the passengers on the vehicle.

In another aspect, the passenger vehicle is an aircraft and the onboard management system is a sub-system of an IFE system installed on the airplane. In such case, the onboard entertainment system is IFE. In still another feature, the IFE system may comprise an in-seat display system wherein the imaging device is integrated into the in-seat display system.

In another feature, the health data includes vital information of the passenger, including one or more of the following: pulse rate, respiration rate, body temperature.

In still another aspect, the images comprise live streaming video. In yet another feature, the images comprise individual images captured and transmitted on-demand.

In another aspect of the health monitoring system, the medical information includes a health condition of the passenger from a medical diagnosis based on the health data. Furthermore, the health condition may be a disease, a sickness, a psychological condition, and/or a state of consciousness. In still another feature, the medical information may include a treatment to be administered to the passenger.

In another aspect of the health monitoring system, the onboard management system may further comprise a video-audio device in addition to the imaging device. The health monitoring system may be further configured to enable live video chat between the video-audio device and a remotely located medical caregiver using the telemedical monitoring system. For instance, the video-audio device may be an in-seat display system of an onboard entertainment system installed on the vehicle, or a portable personal electronic device having a camera, two-way audio (e.g., a microphone and a speaker), and a display.

In another aspect, the onboard management system may be configured to provide an alert to a crew member when the medical information received from the telemedical monitoring system indicates the passenger requires attention from a crew member. For instance, the onboard management system may be configured to sound an audio alert, and/or display a graphical alert on a display monitor of a crew terminal.

In another aspect, the medical information can be used to determine whether a passenger needs to be quarantined, either onboard, or upon arrival at a station or airport, because the passenger may have a contagious disease. If it is determined the passenger needs to be quarantined, then the onboard management system and/or telemedical monitoring system sends a warning to quarantine the passenger to one of a carrier operating the vehicle, authorities responsible for carrying out the quarantine (e.g., a government health agency), and/or authorities at a station at which the vehicle will be arriving.

In still another aspect, the health monitoring system may be configured to prioritize health conditions, such as prioritizing health conditions as being low importance medical treatment, intermediate importance medical treatment, and/or high importance medical treatment. For instance, the health monitoring system is configured where the imaging device captures images of the one or more passengers; and the health monitoring application is configured to analyze image data of the one or more passenger, determine health data regarding the one or more passengers and provide an alert to at least one crew member and/or at least one of the one or more passengers of a priority condition of the health status regarding each the one or more passengers.

For example, for at least one of analysis of health data, alerts of health status, an alert to manage of health status, or the like by a crew member or alerts to one of the one or more passengers, the analysis of the image data includes: low importance of medical treatment requirement (e.g., minor cut, bruise, itchy eyes or skin, non-immobilizing backpain, inflammation of ankles, wrists, joints, or the like), caution importance of medical treatment (e.g., blood pressure elevated above 170/100, excessive bleeding, dizziness, vomiting, migraine headache, or the like), and high alert for medical treatment (e.g., blood pressure above 200/120, loss of consciousness of a passenger of the one or more passengers for an extended period of time, excessive pain, confusion, quarantine, or the like).

In yet another example, the priority position of each passenger in a generated waiting list of the one or more passengers for at least one of analysis of health data, alerts, notification to manage health status, or the like by a crew member or alerts to one of the one or more passengers may be based on a priority position. In one variation of this example, the priority position of polling (e.g., arranging, performing, or the like of the ordering, the requesting, or the like) of analysis of health data, alerts of health status, an alert to management health status or the like by a crew member or to one or more passengers based on low importance of medical treatment, caution importance of medical treatment, and high alert for medical treatment in accordance with/among may be based on or across multiple airlines, multiple carriers, multiple cities, multiple states, multiple countries, origin and/or destination locations, or combinations thereof.

In addition, the priority position may be based on predetermined criteria, such as the importance of the passenger, severity of health condition, severity of contagiousness of health condition. For example, if the pilot is determined to have a health condition, that would be given a higher priority position than a passenger to ensure the safety of the flight. A higher priority position may also be assigned based on an origination of the flight, such as international flights originating from Asia if there have been reported cases in the area of deadly epidemics (risk of Bird/Avian Flu) or Africa (risk of Ebola). Furthermore, an indication of fever as a health condition would thus be accorded a higher priority on an international flight compared to a domestic flight.

A second embodiment of the present invention is a health monitoring system for monitoring a health status of passengers on a passenger vehicle, same or similar as the first embodiment, except that the images are transmitted to the remote telemedical system, and the image analysis of the images to determine health data is performed by the remote telemedical system. In this second embodiment, the health monitoring software application does not need to be configured to analyze the images to determine health data but needs only to enable the onboard management system to perform the other health monitoring functions. Instead, the telemedical monitoring system has a telemedical software application configured to analyze images of a passenger to determine health data regarding the passenger, such as a passenger's vital signs, same or similar to the health monitoring software application of the first embodiment.

In this second embodiment, the health monitoring system is configured to perform the following process to monitor the health of the passengers on the vehicle. The imaging device captures images of the passenger. The imaging device transmits the images to the onboard management system. The onboard management system transmits the images to the telemedical monitoring system. The telemedical monitoring system analyzes the images and determines health data regarding the passenger, such as vital signs, using the telemedical software application, and also analyzes the health data to determine medical information, such as health condition, diagnosis, care, advice and/or treatment. The telemedical monitoring system provides the medical information to the onboard management system via the communication network. The onboard management system receives the medical information from the telemedical monitoring system based on the analysis of the health data by the remote telemedical system.

In additional aspects of the second embodiment, the health monitoring system may include any of the additional aspects and features of the first embodiment.

In a third embodiment, a health monitoring system for monitoring the health status of passengers on a passenger vehicle utilizes a portable telemedical device. For example, the portable telemedical device may be a handheld computing device such as a smartphone, a handheld crew personal electronic device ("PED"), or the like.

The health monitoring system of the third embodiment includes a portable telemedical device. The telemedical device includes a computing device having a computer processor, memory, a display monitor, system software, and a health monitoring software application configured to analyze image data of a passenger to determine health data regarding the passenger. The health monitoring software application may be same or similar to the health monitoring software application of the first embodiment. The telemedical device also has a communication module configured to communicate via a communication network with a remote telemedical monitoring system. The communication module may be a WiFi communication module, a cellular phone communication module (e.g., for ground vehicles, like trains, automobiles, and buses), a radio frequency air-to-ground communication module (e.g., for aircraft), a satellite communication module (e.g., for aircraft or ships), or the like, which can enable direct or indirect communication between the telemedical device and the remote telemedical monitoring system. For instance, an example of indirect communication is described below in which the telemedical device communicates with the telemedical monitoring system via an onboard management system. In other words, the telemedical device communicates directly with the onboard management system which in turn communicates with the telemedical monitoring system.

The remote telemedical monitoring system may be the same or similar to the remote telemedical monitoring system described with respect to the first embodiment.

The third embodiment of a health monitoring system also includes an imaging device in communication with the telemedical device. The imaging device is configured to capture images of the passenger on the vehicle and provide the images to the telemedical device. Same or similar to the first embodiment, the imaging device may be a digital camera which can capture either or both of still images and video images.

In this third embodiment, the health monitoring system is configured to perform the following process to monitor the health of the passengers on the vehicle. The imaging device captures images of the passenger. The imaging device provides the images to the telemedical device. The telemedical device analyzes the images and determines health data regarding the passenger, such a vital signs, using the health monitoring application. The telemedical device transmits the health data to the telemedical monitoring system via the communication network. The telemedical monitoring system analyzes the health data and provides medical information, such as health condition, diagnosis, care, advice and/or treatment, to the onboard management system via the communication network. The telemedical device receives the medical information from the telemedical monitoring system based on the analysis of the health data by the remote telemedical system.

In another aspect of the third embodiment, the imaging device may be integrated into the telemedical device. For instance, the telemedical device may be a personal electronic device, such as a smartphone, a tablet computer, or the like, and the imaging device may be a built-in camera in the personal electronic device.

In still another aspect of the third embodiment, the passenger vehicle may be an aircraft, and the telemedical device may be a vehicle crew handheld computing device (e.g., a PED), and the communication module may be configured to communicate via an air-to-ground communication network such that the telemedical device transmits the health data directly via the air-to-ground communication network.

In another aspect of the third embodiment, the imaging device may be separate from the telemedical device, and the health monitoring system may be configured such that the images are transmitted from the imaging device to the telemedical device.

In another aspect of the third embodiment, the health monitoring system further comprises an onboard management system, and the health monitoring system is configured such that the telemedical device communicates with the telemedical monitoring system via the onboard management system.

In yet another aspect of the third embodiment, the health monitoring system is further configured to enable live video chat between the telemedical device and a remotely located medical caregiver using the telemedical monitoring system. For instance, the telemedical device may include a camera, two-way audio (e.g., a microphone and a speaker), in addition to a display.

In still another feature of the third embodiment, the health monitoring system further comprises an IFE system having an onboard management system in network communication with an in-seat display system, and the imaging device is integrated into the in-seat display system. In such case, the health monitoring system may be configured such that images are wirelessly transmitted from the onboard management system to the telemedical device.

In another aspect of the third embodiment, the health data comprises vital information of the passenger selected from the group consisting of: pulse rate, respiration rate, and body temperature.

In another aspect of the third embodiment, the images may comprise live streaming video. In still another aspect, the images may comprise individual images captured and transmitted on-demand.

In another aspect of the third embodiment, the medical information includes a health condition of the passenger from a medical diagnosis based on the health data. Furthermore, the health condition may be a disease, a sickness, a psychological condition, and/or a state of consciousness. In still another feature, the medical information may include a treatment to be administered to the passenger.

In another feature of the third embodiment, the telemedical device may be configured to send an alert to an onboard management system when the medical information received from the telemedical monitoring system indicates the passenger requires attention from a crew member.

In another aspect of the third embodiment, the medical information can be used to determine whether a passenger needs to be quarantined, either onboard, or upon arrival at a station or airport, because the passenger may have a contagious disease. If it is determined the passenger needs to be quarantined, then the telemedical device, onboard management system and/or telemedical monitoring system sends a warning to quarantine the passenger to one of a carrier operating the vehicle, authorities responsible for carrying out the quarantine (e.g., a government health agency), and/or authorities at a station at which the vehicle will be arriving.

A fourth embodiment of the invention is a health monitoring system for monitoring a health status of passengers on a passenger vehicle, similar to the third embodiment, except that the images are transmitted to the remote telemedical system, and the image analysis of the images to determine health data is performed by the remote telemedical system. In this fourth embodiment, the health monitoring software application does not need to be configured to analyze the images to determine health data but need only enable the telemedical device to perform the other health monitoring functions. Instead, the telemedical monitoring system has a telemedical software application configured to analyze images of a passenger to determine health data regarding the passenger, such as a passenger's vital signs, same or similar to the health monitoring software application of the other embodiments.

In the fourth embodiment, the health monitoring system is configured to perform the following process to monitor the health of the passengers on the vehicle. The imaging device captures images of the passenger. The imaging device provides the images to the telemedical device. The telemedical monitoring system analyzes the images and determines health data regarding the passenger, such as vital signs, using the telemedical software application, and also analyzes the health data to determine medical information, such as health condition, diagnosis, care, advice and/or treatment. The telemedical monitoring system provides the medical information to the telemedical device via the communication network. The telemedical device receives the medical information from the telemedical monitoring system based on the analysis of the health data by the remote telemedical system.

In additional aspects of the fourth embodiment, the health monitoring system may include any of the additional aspects and features of the third embodiment.

A fifth embodiment of the present invention is directed to a method of monitoring the health status of one or more passengers on a passenger vehicle utilizing an onboard management system. This method may be performed by any of the first and second embodiments described herein. The method includes an imaging device capturing images of a passenger on the vehicle. The images are transmitted to an onboard management system. The onboard management system transmits one or more of (a) the images and (b) health data determined by analyzing the images, to a remote telemedical monitoring system. Accordingly, the method encompasses a process in which the images are transmitted to the remote telemedical monitoring system and the remote telemedical monitoring system analyzes the images to determine health data, and also a process in which the images are analyzed by the onboard management system to determine health data. Next, the onboard management system receives from the telemedical monitoring system medical information regarding the passenger based on an analysis by the telemedical monitoring system of the one or more of (a) the images and (b) the health data.

In another aspect of the fifth embodiment, the method is directed to the onboard management system analyzing the images to determine health data. Thus, the method further comprises the onboard management system analyzing the images and determining health data based on the images using a health monitoring application. Then, the onboard management system transmits the health data to the telemedical monitoring system.

In still another aspect of the fifth embodiment, the method is directed to the telemedical monitoring system analyzing the images and determining health data. In this case, the method further comprises the onboard management system transmitting the images to the telemedical monitoring system. In addition, the medical information received from the telemedical monitoring system is based on an analysis of the images by the telemedical monitoring system.

In additional aspects of the fifth embodiment, the method may include any of the additional aspects and features of the first and second embodiments.

A sixth embodiment of the present invention is directed to another method of monitoring the health status of one or more passengers on a passenger vehicle, utilizing the portable telemedical device. This method may be performed by any of the third and fourth embodiments described herein. The method includes an imaging device capturing images of a passenger on the vehicle. The telemedical device transmits one or more of (a) the images and (b) health data determined by analyzing the images, to a remote telemedical monitoring system. Hence, the method encompasses a process in which the images are transmitted to the remote telemedical monitoring system and the remote telemedical monitoring system analyzes the images to determine health data, and also a process in which the images are analyzed by the telemedical device to determine health data. Next, the telemedical device receives from the telemedical monitoring system medical information regarding the passenger based on an analysis by the telemedical monitoring system of the one or more of (a) the images and (b) the health data.

In another aspect of the sixth embodiment, the method is directed to a process in which the telemedical device analyzes the images to determine health data using a health monitoring software application. Thus, the method further comprises the telemedical device analyzing the images and determining health data based on the images using a health monitoring software application. Then, the telemedical device transmits the health data to the telemedical monitoring system.

In still another aspect of the sixth embodiment, the method is directed to a process in which the telemedical monitoring system analyzes the images and determines health data. In this case, the method further comprises the telemedical device transmitting the images to the telemedical monitoring system. Then, the medical information received from the telemedical monitoring system is based on an analysis of the images by the telemedical monitoring system.

In additional aspects of the sixth embodiment, the method may include any of the additional aspects and features of the third and fourth embodiments, as described herein.

BRIEF DESCRIPTION OF THE DRAWINGS

The foregoing and other aspects of embodiments are described in further detail with reference to the accompanying drawings, wherein like reference numerals refer to like elements and the description for like elements shall be applicable for all described embodiments wherever relevant, wherein.

DETAILED DESCRIPTION

Figure 1:
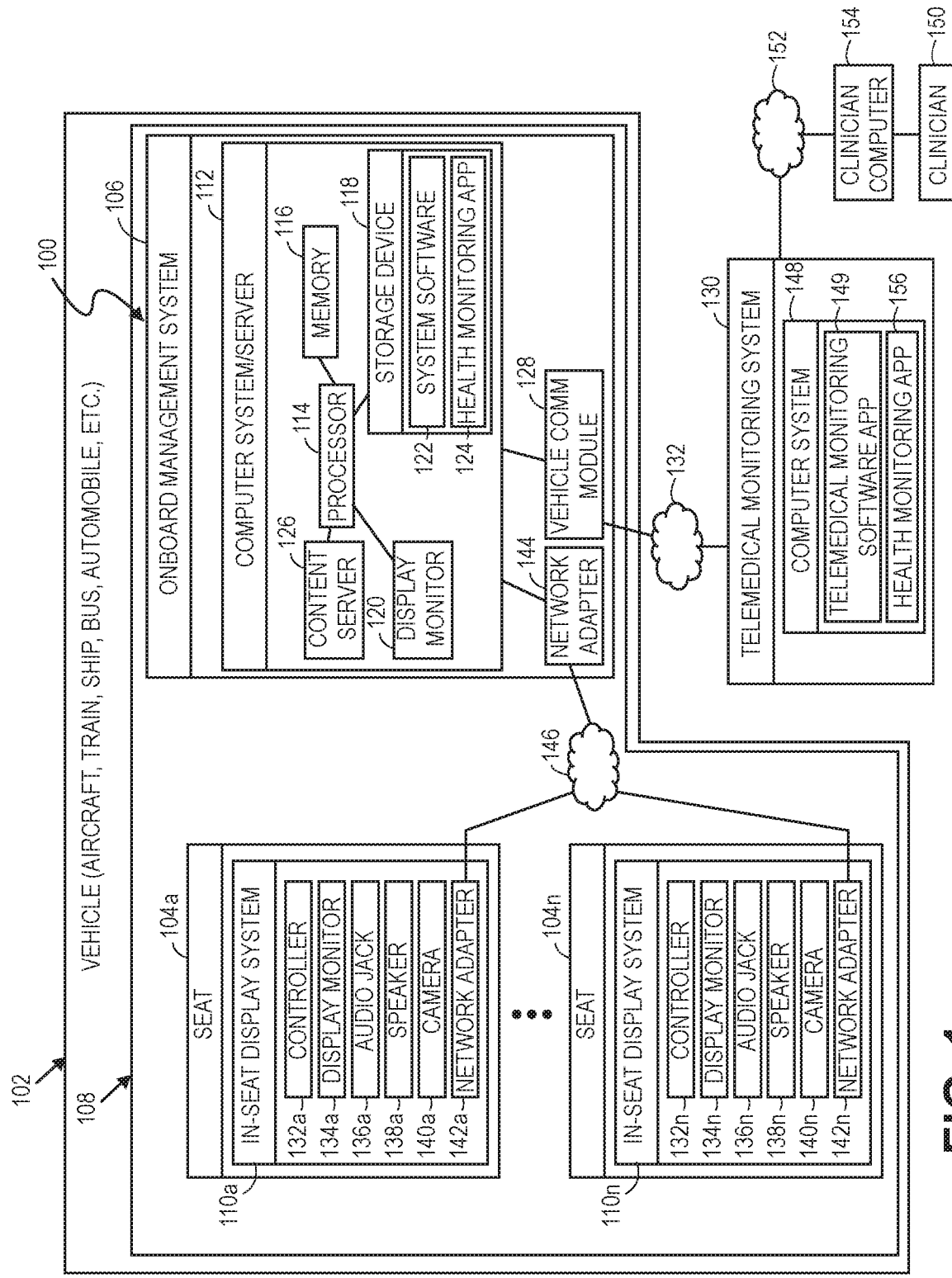
FIG. 1 is a block schematic diagram of a system for monitoring the health status of one or more passengers on a passenger vehicle utilizing an onboard management system, according to one embodiment of the present invention.
Figure 8:
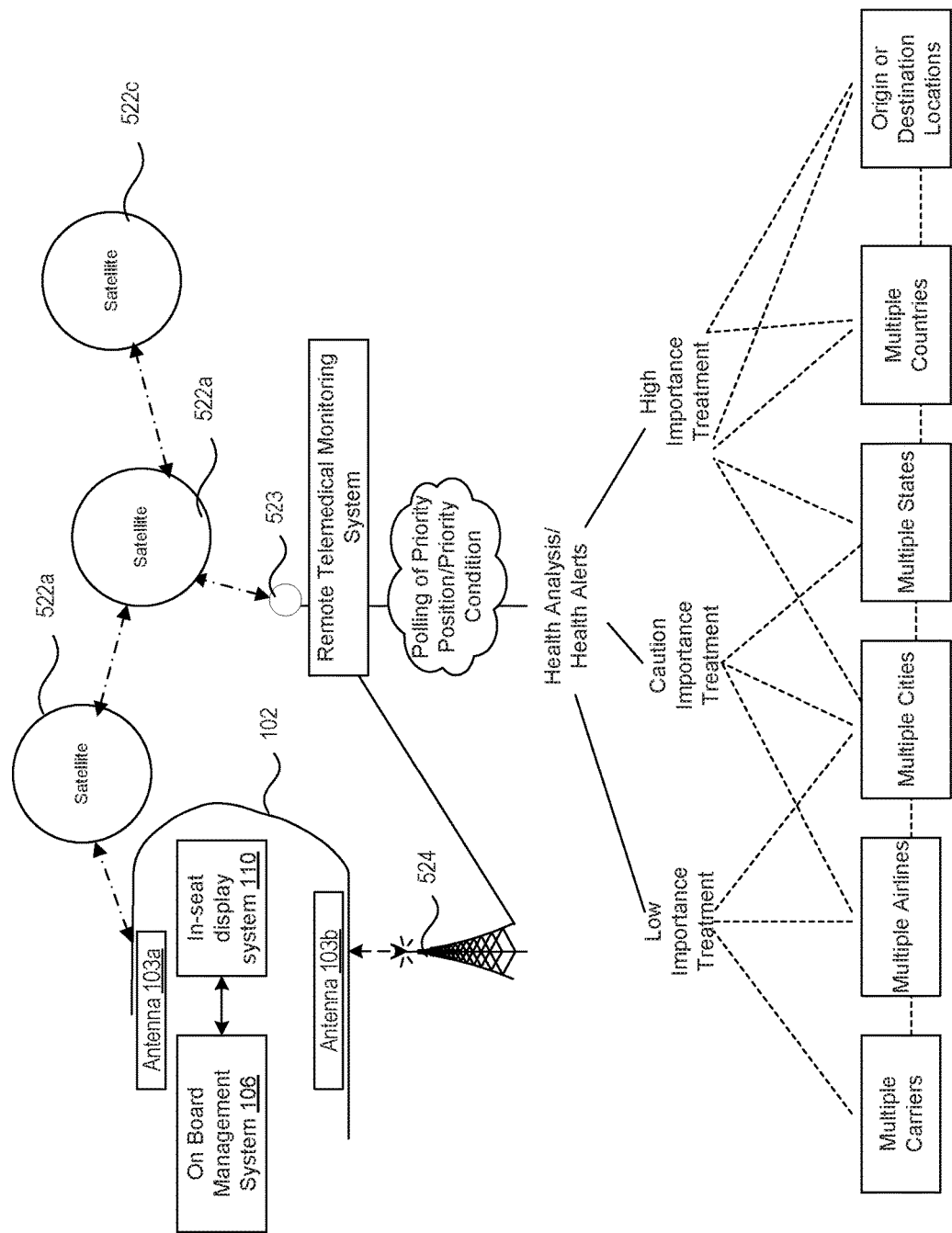
FIG. 8 is a block diagram of an assignment of a priority position and a priority condition for monitoring health status of one or more passengers of a passenger vehicle, according to an embodiment of the present invention.

The present invention is directed to systems and methods for monitoring the health status of passengers on a passenger vehicle. Referring to FIG. 1, a schematic diagram of one embodiment of a health monitoring system 100 for a passenger vehicle 102 is illustrated. The passenger vehicle 102 may be any suitable passenger vehicle, including an aircraft, train, bus, ship, boat, automobile, etc. The vehicle 102 has a plurality of passenger seats 104a-104n. In one example, (as illustrated in FIG. 8), the vehicle 102 (e.g., an airplane) has antenna 103a that communicates with satellites 522a, 522b, and 522c and has antenna 103b that communicates through ground terminal 524. Furthermore, as referred in FIG. 8, Satellites 522a, 522b, 522c receive information from a remote telemedical monitoring system 130 through antenna 523 for vehicle 102 (e.g., an airplane). In one example, remote telemedical monitoring system 130 establishes polling priority position/priority condition based on importance of treatment (e.g., low, caution, and high) across multiple carriers, multiple airlines, multiple cities, multiple states, multiple countries, and origin/destination locations or combinations thereof.

An onboard management system 106 is installed on the vehicle 102. The onboard management system 106 is a computerized system for managing and controlling various passenger systems, such as an onboard entertainment system, passenger service calls, internet networking (e.g., onboard WiFi), etc. For example, the onboard management system 106 may be part of an onboard entertainment system 108, such as an IFE for an aircraft, for providing video and audio entertainment to an in-seat display system 110 installed at each seat 104, and/or at common/shared display systems 110 installed throughout the vehicle (e.g., wall or ceiling mounted display systems viewable by multiple passengers). The onboard management system 106 includes a computer system 112 which may be a computer server. The computer system 112 includes a computer processor 114, memory 116, a storage device 118, a display monitor 120, system software 122 stored on the storage device 118, and a health monitoring software application 124 stored on the storage device 118. The computer system 112 may also have a content storage device or server 126 for storing and distributing media content (e.g., movies, TV shows, music, games, etc.) for providing in-flight entertainment content to each of the in-seat display systems 110.

The onboard management system 106 also has a vehicle communication module 128 operably coupled to the computer system 112. The vehicle communication module 128 is configured to communicate with off vehicle communication systems, including a remote telemedical monitoring system 130. The vehicle communication module 128 may be any suitable communication module for providing communication with a communication network 132 to communicate with the remote telemedical monitoring system 130. For instance, the vehicle communication module 128 may be any suitable communication module for the type of vehicle 102 and communication mode needed to communicate with the telemedical monitoring system 130. For instance: for ground vehicles such as trains, buses and automobiles, the vehicle communication module 128 may be a cellular phone communication module; for aircraft the vehicle communication module 128 may be a radio frequency air-to-ground communication module or satellite communication module; and for ships the vehicle communication module 128 may be a radio frequency communication module, cellular communication module or satellite communication module. The communication module 128 may also be multi-mode such that it can operate in two or more of the aforementioned communication modes. Alternatively, the onboard management system 106 may have multiple communication modules 128, such as two or more of the aforementioned communication modules, in order to communicate using different communication modes.

The onboard management system 106 also has a network adapter 144 to communicate with the in-seat display systems 110 via a communication network 146. The communication network 146 is any suitable communication network, including a LAN, WAN, wireless network, or any combination thereof, and may include any appropriate router, switch, access point, or combination thereof.

The communication network 146 may include any suitable communication network including a proprietary network, LAN, WAN, cellular network, wireless network, the internet, and/or other suitable network, or any combination thereof.

Each seat 104 has a respective in-seat display system 110. The in-seat display system 110 is part of the onboard entertainment system 108 (e.g., an in-flight entertainment system "IFE"). The in-seat display system 110 includes a controller 132 for a passenger to control the in-seat display system 110, including a display monitor 134, an audio jack 136, a speaker 138 and a camera 140. The camera 140 may be used as the imaging device for the health monitoring system 100. The camera 140 has a field of view directed at the passenger in the seat 104 so that it can capture images of the passenger and provide the images to the onboard management system 106. The camera 140 may be any suitable digital camera having a digital image capture device, such as a CCD or CMOS. The camera 140 may be adjustable to move the field of view or fixed (e.g., using a wide angle lens, the field of view can cover all or most of the seat 104). The camera 140 is capable of capturing video and still images. Moreover, the cameras 140 functioning as imaging devices for the health monitoring system 100 may also include additional cameras 140x installed throughout the passenger vehicle, such as security cameras. The cameras 140x are configured to transmit images to the onboard management system 106 via the communication network 146.

The in-seat display system 110 may also include additional features, such as charging port(s), a service call button, etc. The audio jack 136 is configured to interface with a headset having audio earphones and a microphone in order to provide for two-way audio. The in-seat display system 110 for each seat 104 may be installed in the seatback of the seats 104. Alternative to in-seat installations, the display systems 110 may be mounted on cabin walls, deployable from an armrest, etc. The display monitor 134 may be a basic monitor, such as an LCD, OLED monitor, or a smart monitor. For instance, a smart monitor has its own computing device, data storage, network communication adapter (e.g., a wireless communication module or wired networking module) and software applications which enable the smart monitor to establish a network connection to other devices, and to play audio/video media and/or run other software applications such as a game, internet browser, texting applications, or other applications.

The in-seat display systems 110 also have network adapters 142 so that they are in network communication with the onboard management system 106 via the communication network 146.

The health monitoring system 100 primarily utilizes images to determine health data (e.g., vital signs) of the passengers, such that health data (e.g., vital signs of a passenger) is obtained without physically contacting the passengers (contactless), as opposed to typical vital sign devices which physically contact a person. Accordingly, the health monitoring software application 124 is a customized software application which programs the computer system 112 to analyze images of a passenger to determine health data regarding the passenger, such as a passenger's vital signs. The health monitoring software application may utilize the methods as disclosed in U.S. Published Patent Application No. 2018/0310844 A1 and U.S. Published Patent Application No. 2018/0220939 A1, or any other suitable system or method to obtain health data of a person from images.

The remote telemedical monitoring system 130 is any suitable telehealth (also referred to as telemedicine) system which provides medical information via telecommunication. The telemedical monitoring system 130 includes a computer system 148 which may be a computer server. The telemedical monitoring system 130 has hardware and a telemedical monitoring software application 149 to allow it to remotely receive health data, such as vital signs and symptoms of a passenger, and analyze the health data to determine medical information regarding the passenger. The telemedical monitoring software application 149 may include a diagnosis software application having diagnostic algorithms to analyze the health data to determine medical information, and/or it can provide the health data to a clinician 150, either remote to the system 130 on a clinician computer 154 via communication network 152 or local to the system 130 on a clinician computer or directly on the computer system 148. The telemedical monitoring system 130 allows a clinician and a patient (a passenger or caregiver with the passenger) to have remote communication of health data, including vital information and symptoms of the patient, as well enabling the telemedical monitoring system 130 to provide medical information. The medical information determined and provided by the telemedical monitoring system 130 includes a health condition (i.e., a diagnosis), care, advice and/or treatment as determined by the automated software clinician.

The medical information determined by the telemedical monitoring system 130 may include a health condition of the passenger from a medical diagnosis based on the health data. For instance, the health condition may be a disease, a sickness, a psychological condition, and/or a state of consciousness. Furthermore, the medical information may include a treatment to be administered to the passenger.

In addition, the telemedical monitoring system 130 enables two-way, live communication, including audio and video, between the clinician 150 and the passenger or onboard caregiver via the onboard management system 106 and/or in-seat display system 110.

Figure 2:
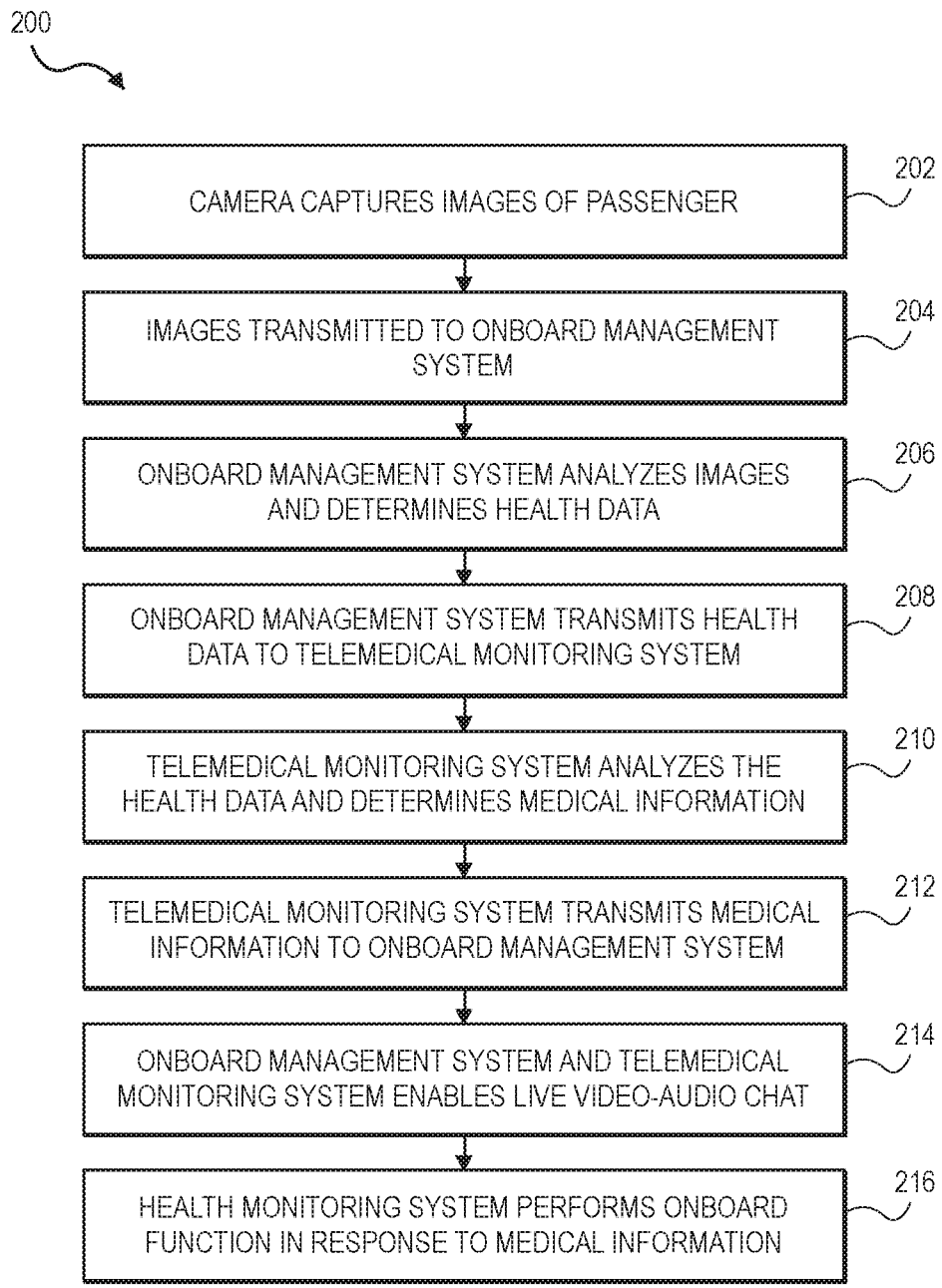
FIG. 2 is a flow chart of a first method for monitoring the health status of one or more passengers on a passenger vehicle using the system of FIG. 1, according to one embodiment of the present invention.

FIG. 2 illustrates an exemplary flow chart for a first method 200 for monitoring the health status of one or more passengers on a passenger vehicle using the health monitoring system 100. The first method 200 is directed to a method in which the images are analyzed by the onboard management system 106 using the health monitoring software application 124. At step 202 of the method 100, the camera 140 captures images of a passenger on the vehicle 102. For instance, the camera 140a of the in-seat display system 110a at seat 104a captures images of a passenger sitting in seat 104a. The images may be streaming video, or still images on-demand.

At step 204, the images are transmitted to the onboard management system 106 via the communication network 146 using the network adapter 142a and the network adapter 144. At step 206, the onboard management system 106 analyzes the images using the computer system 112 and the health monitoring software application 124 and determines health data regarding the passenger. The health data includes vital signs of the passenger, including one or more of pulse rate, respiration rate, and body temperature. The health data may also include a state of consciousness, anxiety, restlessness, panic and any other health information of a passenger which can be determined from analyzing images of the passenger. For instance, the health monitoring software application may determine that a passenger is sleeping, anxious, restless, or in a panic by analyzing the images for physical signs of these health conditions.

At step 208, the onboard management system 106 transmits the health data to the remote telemedical monitoring system 130 using the vehicle communication module 128 via the communication network 132. At step 210, the telemedical monitoring system 130 determines medical information regarding the passenger, as described above. The medical information determined by the telemedical monitoring system 130 based on the health data includes one or more of a health condition (i.e., a diagnosis), care, advice and/or treatment.

At step 212, the telemedical monitoring system 130 transmits the medical information to the onboard management system 106, and the onboard management system 106 receives from the telemedical monitoring system the medical information regarding the passenger.

At step 214, the onboard management system 106 and telemedical monitoring system 130 enable live video and audio chat between in-seat display system 110 and a remotely located clinician 150 using either a clinician computer 154 or the telemedical monitoring system 130. The display monitor 134 displays video of the clinician 150 and the speaker or a headset connected to the audio jack 136 provides audio from the clinician. Similarly, a display monitor and audio device of the clinician computer 154 or the telemedical monitoring system 130 provide live streaming video and audio from the in-seat display system 110. Alternatively, the onboard vehicle end of the live video and audio chat may be provided on the computer system 112 (e.g., a crew terminal of the onboard management system 106).

In addition, the health monitoring system 100 may also be configured to perform certain functions using the onboard management system 106 and in-seat display systems 110 in response to the medical information. For example, when the medical information indicates that the passenger is sleeping or sleepy, the onboard management system 106 sends a message to the in-seat display system 110 for the passenger to turn the display monitor 134 off, to turn the audio volume down or off, to adjust the seat of the passenger (e.g., recline the seat) and/or to dim or turn off a reading light and/or ambient light at the passenger's seat. The onboard management system 106 can also send a message to a crew member that a passenger is sleeping and instruct not to disturb the passenger. As another example, when the medical information indicates that the passenger is in a panic, the onboard management system 106 can display and/or send a message to a crew member, such as at a crew terminal or handheld crew PED to check on the passenger. In addition, when the medical information indicates that a passenger has an above normal temperature, the onboard management system 106 and/or in-seat display system 110 can adjust the air conditioning and/or air vents at the passenger's seat. When the medical information for some or all of the passengers indicates they have an above normal temperature, the onboard management system 106 can adjust the vehicle cabin temperature. As another example, when the medical information indicates that a passenger is drunk, the onboard management system 106 can display and/or send a message to a crew member, such as at a crew terminal or handheld crew PED, to stop serving alcoholic beverages to such passenger. Accordingly, at step 216 of the method 100, the health monitoring system 100 performs an onboard function in response to the medical information.

Figure 3:
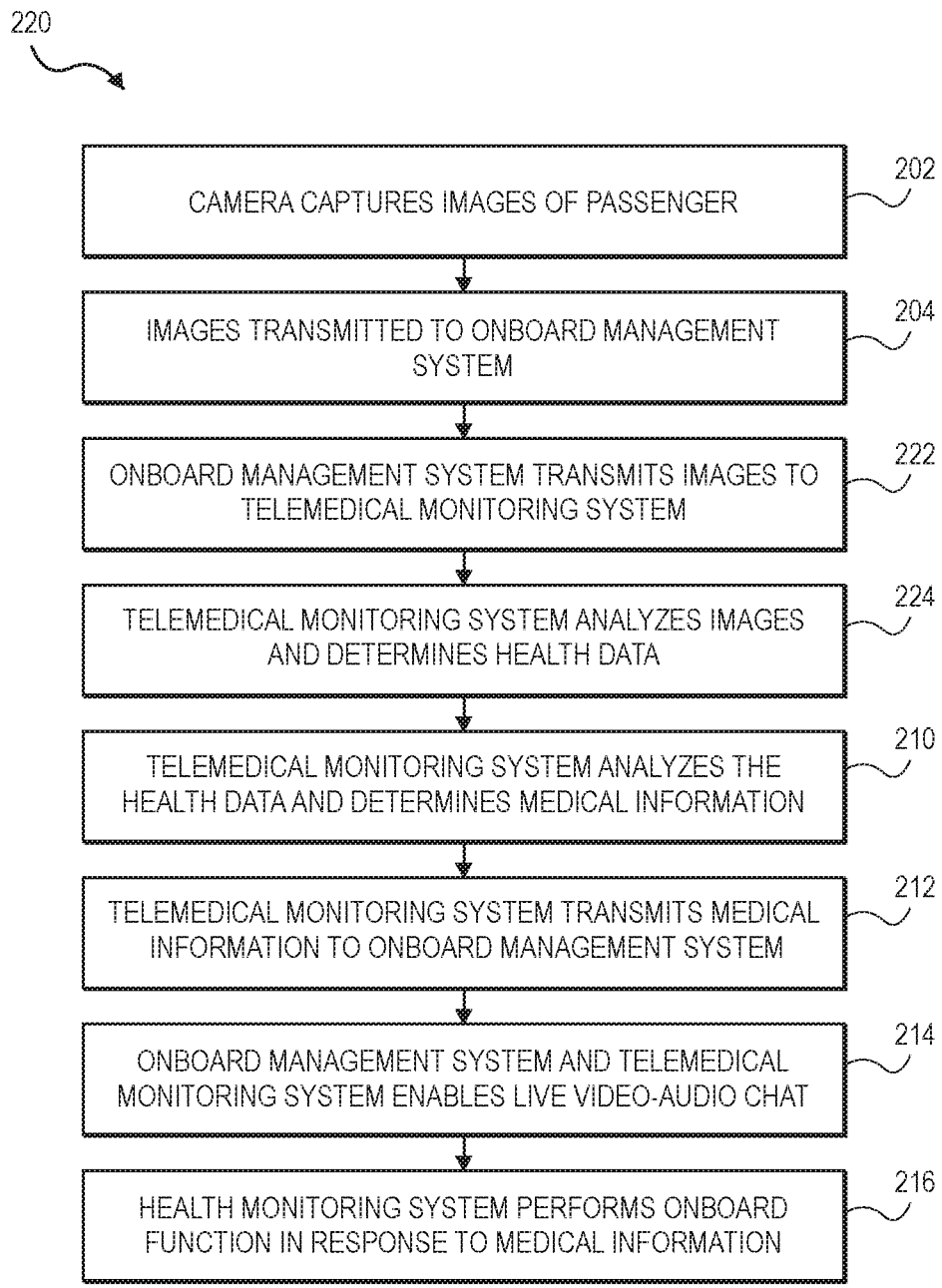
FIG. 3 is a flow chart of a second method for using the system of FIG. 1 for monitoring the health status of one or more passengers on a passenger vehicle, according to one embodiment of the present invention.

FIG. 3 illustrates an exemplary flow chart for a second method 220 for monitoring the health status of one or more passengers on a passenger vehicle using the health monitoring system 100. The second method 220 is directed to a method in which the images are transmitted to the telemedical monitoring system 130 and analyzed by the telemedical monitoring system 130 to determine health data using a health monitoring software application 156. In such case, the health monitoring software application 124 of the onboard management system 106 does not need this functionality. The health monitoring software application 156 of the telemedical monitoring system 130 is similar to the health monitoring software application 124 of the onboard management system 106, and the description of the health monitoring software application 124 applies equally to the health monitoring software application 156. In addition, like reference numerals in the methods 200 and 220 refer to like elements and the description for like elements shall be applicable for both method embodiments, wherever relevant. Steps 222 and 224 are the different steps in the second method 220 compared to the first method 200. At step 222 of method 220, the onboard management system 106 transmits the images to the telemedical monitoring system 130 via the communication network 132. At step 224, the telemedical monitoring system 130 analyzes the images using the computer system 148 and the health monitoring software application 156 and determines health data regarding the passenger. The health data is the same health data as determined using the health monitoring software application 124, as described herein. It is understood that the second method 220 can include any of the aspects and/or features described for the first method 200.

Figure 4:
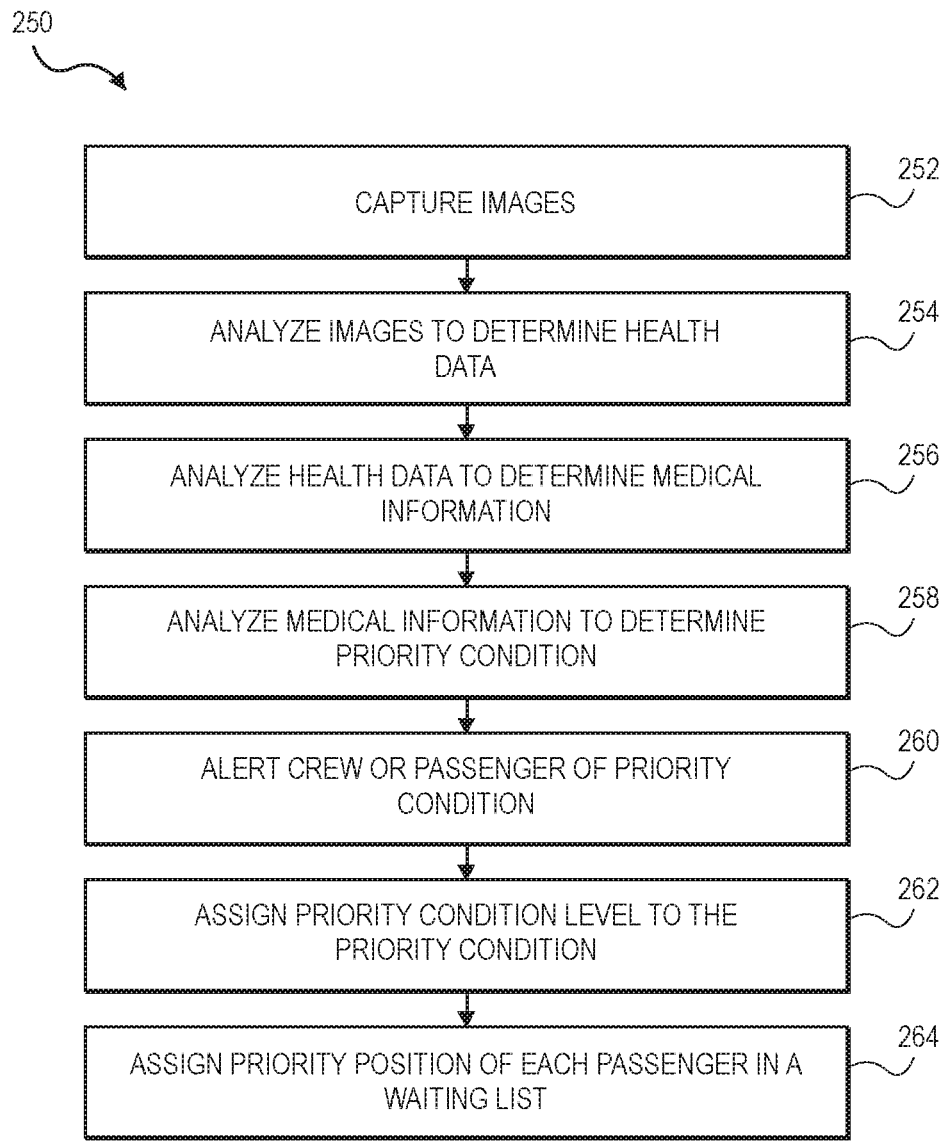
FIG. 4 is a flow chart of a method for the using the system of FIG. 1 to prioritize health conditions of passengers, according to one embodiment of the present invention.

Referring now to FIG. 4, a method 250 for prioritizing health conditions as being low importance medical treatment, intermediate importance medical treatment, and/or high importance medical treatment is illustrated. In this case, the health monitoring system 100 is configured to prioritize health condition and assign a priority condition of the health status of a passenger. The health monitoring system 100 is configured such that the camera 140 captures images of the one or more passengers. The health monitoring software application 156 is configured to analyze the image data of the one or more passenger, determine health data regarding the one or more passengers and provide an alert to at least one crew member and/or at least one of the one or more passengers of a priority condition of the health status regarding each the one or more passengers.

For example, for at least one of analysis of health data, alerts of health status, an alert to manage of health status, or the like by a crew member or alerts to one of the one or more passengers, the analysis of the image data includes a priority condition level, such as low importance of medical treatment requirement (e.g., minor cut, bruise, itchy eyes or skin, non-immobilizing backpain, inflammation of ankles, wrists, joints, or the like), caution importance of medical treatment (e.g., blood pressure elevated above 170/100, excessive bleeding, dizziness, vomiting, migraine headache, or the like), and high alert for medical treatment (e.g., blood pressure above 200/120, loss of consciousness of a passenger of the one or more passengers for an extended period of time, excessive pain, confusion, quarantine, or the like).

In one example, the health monitoring software application 156 assigns a priority position of each passenger in a generated waiting list of the one or more passengers for at least one of analysis of health data, alerts, notification to manage health status, or the like by a crew member or alerts to one of the one or more passengers based on a priority position. In another example, the priority position of polling (e.g., arranging, performing, or the like of the ordering, the requesting, or the like) of analysis of health data, alerts of health status, an alert to management health status or the like by a crew member or to one or more passengers based on low importance, caution importance of medical treatment, and high alert for medical treatment in accordance with/among may be based on or across multiple airlines, multiple carriers, multiple cities, multiple states, multiple countries, origin and/or destination locations, or combinations thereof (see FIG. 8 for additional details).

In addition, the priority position may be based on predetermined criteria, such as the importance of the passenger, severity of health condition, severity of contagiousness of health condition. For example, if the pilot is determined to have a health condition, that would be given a higher priority position than a passenger to ensure the safety of the flight. A higher priority position may also be assigned based on an origination of the flight, such as international flights originating from Asia if there have been reported cases in the area of deadly epidemics (risk of Bird/Avian Flu) or Africa (risk of Ebola). Furthermore, an indication of fever as a health condition would thus be accorded a higher priority on an international flight compared to a domestic flight.

As shown in FIG. 4, the method 250 includes a step 252 in which the health monitoring system 100 captures images of a passenger using the camera 140. At step 254, the health monitoring system 100 analyzes the images and determines health data, as described herein. At step 256, the health data is analyzed to determine medical information as described herein. At step 258, the health monitoring system 100 analyzes the medical information and determines a priority condition of the health status of the passenger. At step 260, the health monitoring system 100 alerts one of a crew member or a passenger of the priority condition. At step 262, the health monitoring system 100 assigns a priority condition level to the priority condition of the passenger. At step 264, the health monitoring system 100 assigns a priority position of each passenger in a generated waiting list of the passengers for at least one of analysis of health data, alerts, notification to manage health status, or the like by a crew member or alerts to one of the one or more passengers based on a priority position.

Figure 5A:
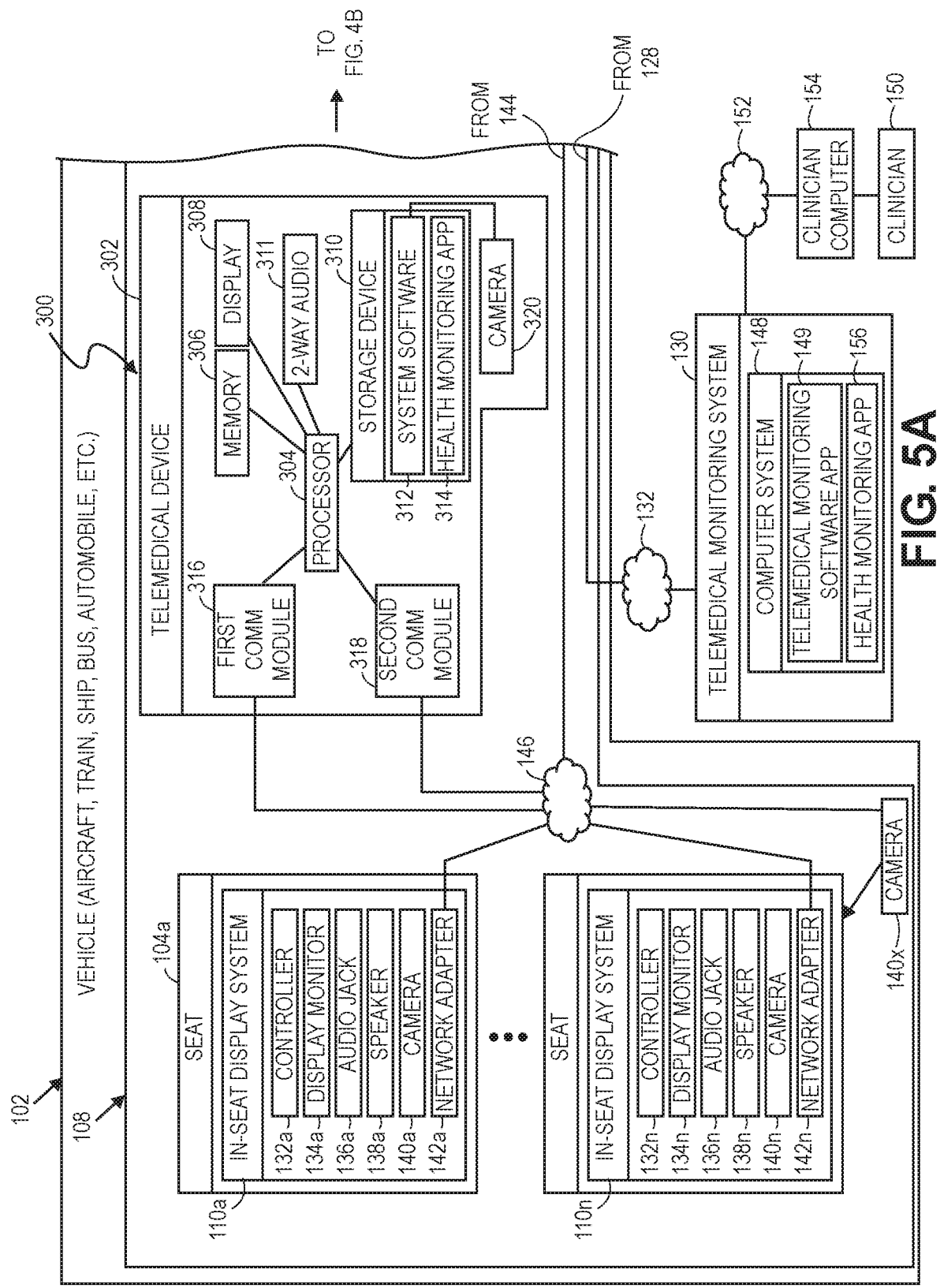
FIGS. 5A-5B is a block schematic diagram of a system for monitoring the health status of one or more passengers on a passenger vehicle utilizing a portable telemedical device, according to one embodiment of the present invention.
Figure 5B:
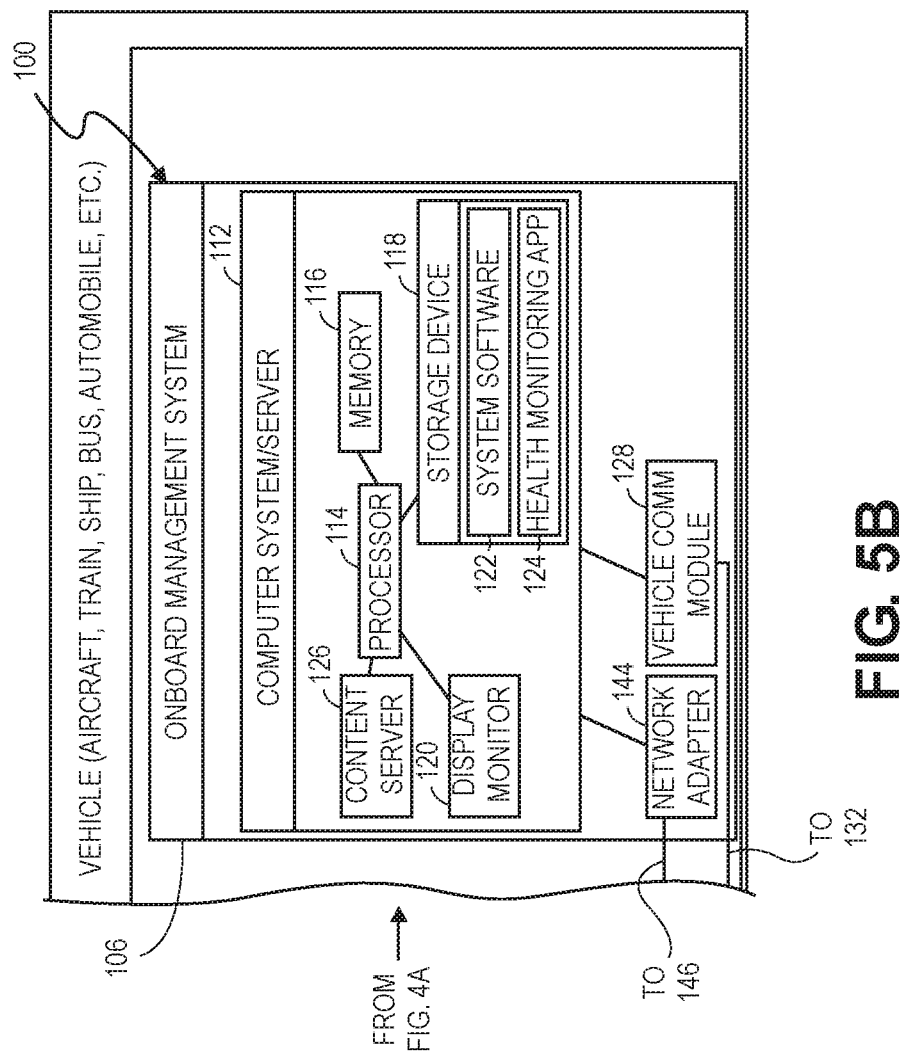

Turning to FIGS. 5A-5B, a schematic diagram of another embodiment of a health monitoring system 300 for a passenger vehicle 102 is illustrated. The health monitoring system 300 is similar to the health monitoring system 100 of FIG. 1, except that the health monitoring system 300 utilizes a portable, telemedical device 302. As described herein, the telemedical device 302 can perform the functions of the onboard management system 106 in the health monitoring system 100 (in which case, the health monitoring system 300 does not need to have the onboard management system 106), and/or it can function together with onboard management system 106. The health monitoring system 300 is depicted in FIGS. 5A-5B with the onboard management system 106, with the understanding that in certain embodiments, it is not needed and is not a part of the health monitoring system 300. Again, like reference numerals in the health monitoring system 300 and the health monitoring system 100 refer to like elements, and the description for like elements shall be applicable for both system embodiments, wherever relevant in FIGS. 5A-5B.

The telemedical device 302 is a portable computing device. For instance, the telemedical device 302 may be a handheld computer, having a form factor of a smartphone or table computer. Indeed, the telemedical device 302 may comprise a smartphone, tablet computer, handheld vehicle PED, or the like. The telemedical device 302 comprises a processor 304, memory 306, a display 308 (e.g., LCD, OLED, etc.), a storage device 310, two-way audio 311 (e.g., a speaker, microphone, and/or two way audio jack for connecting a microphone/headphone headset), system software 312 stored on the storage device 310, and a health monitoring software application 314 stored on the storage device 310.

The telemedical device 302 has a first communication module 316 integrated into the telemedical device 302. The first communication module 316 is configured to communicate with off vehicle communication systems, including the remote telemedical monitoring system 130. The vehicle communication module 316 may be any suitable communication module for providing communication via a communication network 132 to communicate with the remote telemedical monitoring system 130. For instance, the vehicle communication module 316 may be any suitable communication module for the type of vehicle 102 and communication mode needed to communicate with the telemedical monitoring system 130. For instance: for ground vehicles such as trains, buses and automobiles, the vehicle communication module 316 may be a cellular phone communication module; for aircraft the vehicle communication module 316 may be a radio frequency air-to-ground communication module or satellite communication module; and for ships the vehicle communication module 316 may be a radio frequency communication module, cellular communication module or satellite communication module. The communication module 316 may also be multi-mode such that it can operate in two or more of the aforementioned communication modes. Alternatively, the telemedical device 302 may have multiple communication modules 316 for communicating with off vehicle communication systems, such as two or more of the aforementioned communication modules, in order to communicate using different communication modes.

The telemedical device 302 also has a second communication module 318 integrated into the telemedical device 302. The second communication module 318 is configured to communicate with the onboard management system 106 via the communication network 146. The second communication module 318 may be the same or similar to the network adapter 144. In the case that the health monitoring system 300 is configured without an onboard management system 106, the second communication module 318 may be unnecessary.

The health monitoring system 300 may be configured in several ways for having the images analyzed to determine health data. In a first way, the telemedical device 302 itself analyzes the images and determines health data. In this case, the health monitoring software application 314 may be the same or similar to the health monitoring software application 124 of the health monitoring system 100. In a second way, the telemedical device 302 transmits the images to the onboard management system 106, and onboard management system 106 analyzes the images and determines health data using the health monitoring software application 124 of the onboard management system 106. In this case, the health monitoring software application 124 of the onboard management system 106 is configured to perform the image analysis, as described above. In another way, the images are transmitted to the telemedical monitoring system 130 (which may be via the onboard management system 106, as described herein), and the telemedical monitoring system 130 analyzes the images and determines health data using the health monitoring software application 156. In this way, the health monitoring software application 156 is configured to perform the image analysis, as described herein.

The health monitoring system 300 also has a camera 320 which functions as the imaging device for the health monitoring system 300. The camera 320 is same or similar to the camera 140 described herein, and the description of the camera 140 applies equally to the camera 320. Alternatively, the health monitoring system 300 may utilize the cameras 140a-140n, and 140x as the imaging device. In such case, the images may be transmitted from the cameras 140a-140n, and 140x to any one or more of the telemedical device 302 (e.g., via the communication network 146 and/or onboard management system 106), the onboard management system 106 (e.g., via the communication network 146), and/or the telemedical monitoring system 130 (e.g., via the communication network 146, onboard management system 106, telemedical device 302, and/or communication network 132).

The telemedical device 302 and telemedical monitoring system 130 are configured to enable two-way, live communication, including audio and video, between the clinician 150 and the passenger or onboard caregiver via the telemedical device 302 (in some cases, via the onboard management system 106).

Figure 6:
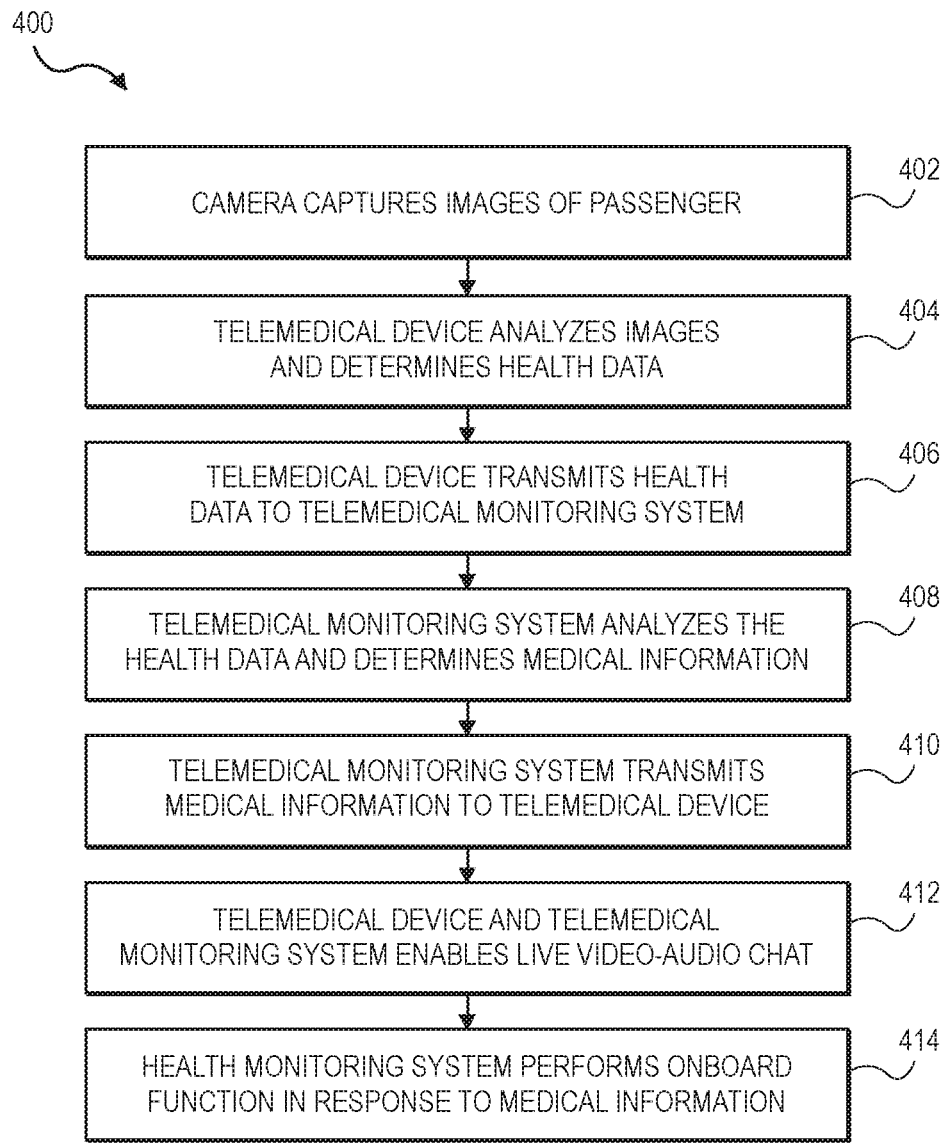
FIG. 6 is a flow chart of a third method for using the system of FIG. 2 for monitoring the health status of one or more passengers on a passenger vehicle, according to one embodiment of the present invention.

FIG. 6 illustrates an exemplary flow chart for a third method 400 for monitoring the health status of one or more passengers on a passenger vehicle 102 using the health monitoring system 300. The third method 400 is directed to a method in which the images are analyzed directly by the telemedical device using the health monitoring software application 124. At step 402 of the method 400, the camera 320 captures images of a passenger on the vehicle 102. The images may be streaming video, or still images on-demand.

At step 404, the telemedical device 302 uses the health monitoring software application 314 to analyze the images to determine health data regarding the passenger. The health data includes vital signs of the passenger, including one or more of pulse rate, respiration rate, and body temperature. The health data may also include a state of consciousness, anxiety, restlessness, panic and any other health information of a passenger which can be determined from analyzing images of the passenger. For instance, the health monitoring software application 314 may determine that a passenger is sleeping, anxious, restless, or in a panic by analyzing the images for physical signs of these health conditions.

At step 406, the telemedical device 302 transmits the health data to the remote telemedical monitoring system 130. The telemedical device 302 can transmit the health data to the telemedical monitoring system 130 in several ways. The telemedical device 302 can transmit the health data to the telemedical monitoring system 130 using the first communication module 316 via the communication network 132. Alternatively, the telemedical device 302 can transmit the health data to the telemedical monitoring system 130 by first transmitting the health data to the onboard management system 106 via the communication network 146, and then the onboard management system 106 transmitting the health data to the telemedical monitoring system 130 using the vehicle communication module 128 via the communication network 132.

At step 408, the telemedical monitoring system 130 analyzes the health data and determines medical information regarding the passenger, same as step 210 described above. The medical information determined by the telemedical monitoring system 130 based on the health data includes one or more of a health condition (i.e., a diagnosis), care, advice and/or treatment.

At step 410, the telemedical monitoring system 130 transmits the medical information to the telemedical device 302, and the telemedical device 302 receives from the telemedical monitoring system 130 the medical information regarding the passenger. This can be accomplished in the same various means as the telemedical device 302 transmitting the health data to the telemedical monitoring system 130, except in the other communication direction.

At step 412, the telemedical device 302 and telemedical monitoring system 130 enable live video and audio chat between in-seat display system 110 and a remotely located clinician 150 using either a clinician computer 154 or the telemedical monitoring system 130. The display 308 displays video of the clinician 150 and the two-way audio 311 provides audio from the clinician. Similarly, a display monitor and audio device of the clinician computer 154 or the telemedical monitoring system 130 provide live streaming video and audio from the in-seat display system 110.

In addition, same as the health monitoring system 100, the health monitoring system 300 may also be configured to perform certain functions using the telemedical device 302, onboard management system 106 and in-seat display systems 110 in response to the medical information. For example, when the medical information indicates that the passenger is sleeping or sleepy, the telemedical device 302 sends a message to the in-seat display system 110 (which may be direct or via the onboard management system 106) for the passenger to turn the display monitor 134 off, to turn the audio volume down or off, to adjust the seat of the passenger (e.g., recline the seat) and/or to dim or turn off a reading light and/or ambient light at the passenger's seat. The telemedical device 302 can also send a message to a crew member (which may be direct or via the onboard management system 106) informing the crew member that a passenger is sleeping and instruct the crew member not to disturb the passenger. As another example, when the medical information indicates that the passenger is in a panic, the telemedical device 302 and/or onboard management system 106 can display and/or send a message to a crew member, such as at a crew terminal or handheld crew PED to check on the passenger. In addition, when the medical information indicates that a passenger has an above normal temperature, the telemedical device 302, onboard management system 106 and/or in-seat display system 110 can communicate to adjust the air conditioning and/or air vents at the passenger's seat. When the medical information for some or all of the passengers indicates they have an above normal temperature, the telemedical device 302 and/or onboard management system 106 can communicate to adjust the vehicle cabin temperature. As another example, when the medical information indicates that passenger is drunk, the telemedical device 302 and/or onboard management system 106 can display and/or send a message to a crew member, such as at a crew terminal or handheld crew PED, to stop serving alcoholic beverages to such passenger. Accordingly, at step 414 of the method 400, the health monitoring system 400 performs an onboard function in response to the medical information.

Figure 7:
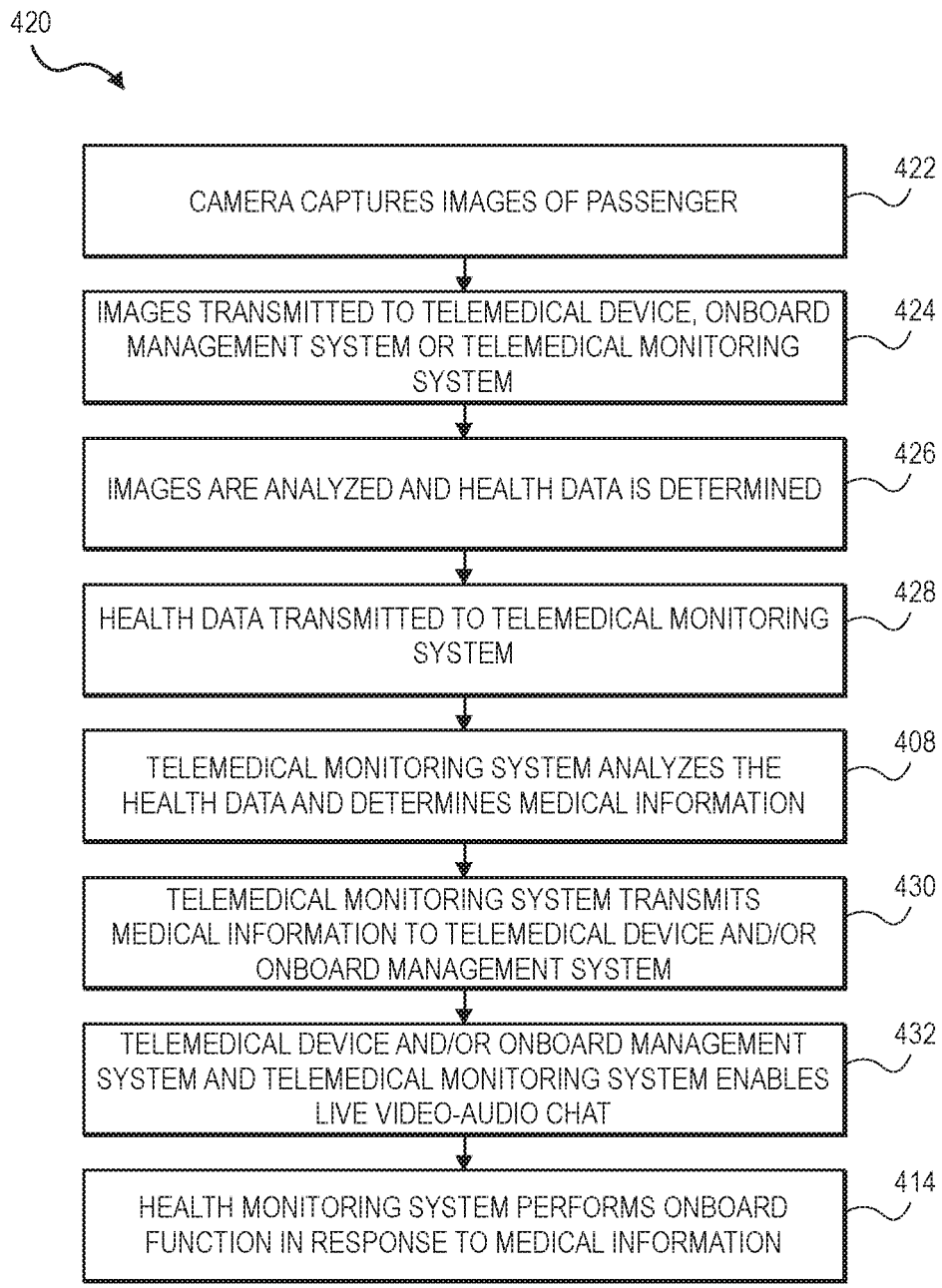
FIG. 7 is a flow chart of a fourth method for using the system of FIG. 2 for monitoring the health status of one or more passengers on a passenger vehicle, according to one embodiment of the present invention.

FIG. 7 illustrates an exemplary flow chart for a fourth method 420 for monitoring the health status of one or more passengers on a passenger vehicle using the health monitoring system 300. The fourth method 420 encompasses the many variations of processes to monitor the health of passengers on a passenger vehicle which can be performed using the health monitoring system 300. For instance, the method 420 illustrates methods in which any one of the cameras 140a-140n, 140x, and/or 320 may capture the images, and any one of the onboard management system 106, the telemedical monitoring system 130, or the telemedical monitoring device 302 can analyze the images to determine health data of the passengers, and the various modes and paths of communication possible. In addition, like reference numerals in the methods 400 and 420 refer to like elements and the description for like elements shall be applicable for both method embodiments, wherever relevant.

At step 422, any one or more of the cameras 140a-140n, 140x and 320 captures images of a passenger on the vehicle 102. At step 424, the images are transmitted to one of the telemedical device 302, onboard management system 106, and/or telemedical monitoring system 130, depending on which one will perform the analysis of the images to determine health data. The images are transmitted using any suitable one or more of the communication devices and/or communication networks of the health monitoring system 300.

At step 426, the images are analyzed, and health data is determined by one of the telemedical device 302, onboard management system 106, and/or telemedical monitoring system 130. In the cases that the telemedical device 302 or onboard management system 106 determine the health data, at step 428, the health data is transmitted to the telemedical monitoring system 130, using any suitable one or more of the communication devices and/or communication networks of the health monitoring system 300. At step 408, the telemedical monitoring system 130 analyzes the health data and determines medical information regarding the passenger, same as step 408 as described regarding FIG. 6.

At step 430, the telemedical monitoring system 130 transmits the medical information to any one of the telemedical device 302, and/or onboard management system 106. At step 432, the health monitoring system 300 enables live video and audio chat between the one of the telemedical device 302 and/or onboard management system 106, and the telemedical monitoring system 130, as described herein.

At step 414 of the method 420, the health monitoring system 400 performs an onboard function in response to the medical information, same as step 414 of the method 400.

Although particular embodiments have been shown and described, it is to be understood that the above description is not intended to limit the scope of these embodiments. While embodiments and variations of the many aspects of the invention have been disclosed and described herein, such disclosure is provided for purposes of explanation and illustration only. Thus, various changes and modifications may be made without departing from the scope of the claims. For example, not all of the components described in the embodiments are necessary, and the invention may include any suitable combinations of the described components, and the general shapes and relative sizes of the components of the invention may be modified. Accordingly, embodiments are intended to exemplify alternatives, modifications, and equivalents that may fall within the scope of the claims. The invention, therefore, should not be limited, except to the following claims, and their equivalents.

What is claimed is:

1. A health monitoring system for monitoring a health status of one or more passengers on a passenger vehicle, the health monitoring system comprising:
    (a) an onboard management system including:
        a computing device having a computer processor, memory, a display monitor, system software, and a health monitoring application; and
        a vehicle communication module configured to communicate with a remote telemedical monitoring system via a communication network; and
    (b) an imaging device in communication with the onboard management system, the imaging device configured to capture images of the one or more passengers on the vehicle and transmit the images to the onboard management system;
    wherein the health monitoring system is configured such that: (1) the imaging device captures images of the one or more passengers; (2) the imaging device transmits the images to the onboard management system; and (3) the onboard management system analyzes the images and determines health data regarding the one or more passengers using a health monitoring application and alerts a crew member and at least one of the one or more passengers of an action to take to manage the health status,
    wherein the health monitoring system is further configured to generate a waiting list used for at least one of an analysis of the images or an alert to the crew member and the at least one of the one or more passengers by assigning priority positions of the one or more passengers in the waiting list based on at least one of an importance of the one or more passengers, a severity of health conditions, or a severity of contagiousness of health conditions.

2. The health monitoring system of claim 1, wherein the onboard management system transmits one or more of (i) the images and (ii) the health data through the health monitoring application to a remote telemedical monitoring system; and (iii) the onboard management system receives from the telemedical monitoring system via the communication network medical information regarding the one or more passengers based on an analysis by the telemedical monitoring system of the one or more of (i) the images and (ii) the health data.

3. The health monitoring system of claim 1, wherein the onboard management system receives from the telemedical monitoring system, via the communication network, medical information regarding the one or more passengers based on an analysis of the images by the telemedical system to determine health data and an analysis of the health data by the telemedical system to determine medical information.

4. The health monitoring system of claim 1, wherein the passenger vehicle is an airplane and the onboard management system is a sub-system of an in-flight entertainment system installed on the airplane.

5. The health monitoring system of claim 4, wherein the in-flight entertainment system comprises an in-seat display system and the imaging device is integrated into the in-seat display system.

6. The health monitoring system of claim 1, wherein the health data comprises vital information of the one or more passengers selected from the group consisting of: pulse rate; respiration rate; and body temperature.

7. The health monitoring system of claim 1, wherein the images comprise one of live streaming video and individual images captured and transmitted on-demand.

8. The health monitoring system of claim 1, wherein the medical information comprises a health condition of the one or more passengers from a medical diagnosis based on the health data selected from the group consisting of: a disease; a sickness; a psychological condition; and a state of consciousness.

9. The health monitoring system of claim 1, wherein the onboard management system further comprises a video-audio device, and the health monitoring system is further configured to enable live video chat between the video-audio device and a remotely located medical caregiver using the telemedical monitoring system.

10. A health monitoring system for monitoring a health status of one or more passengers on a passenger vehicle, the health monitoring system comprising:
(a) a portable telemedical device including:
 a computing device having a computer processor, memory, a display monitor, system software, and a health monitoring application; and
 a communication module configured to communicate via a communication network with a remote telemedical monitoring system; and
(b) an imaging device configured to capture images of the one or more passengers on the vehicle;
wherein the health monitoring system is configured such that: (1) the imaging device captures images of the one or more passengers; and a health monitoring application is configured to analyze image data of the one or more passenger and determines health data regarding the one or more passengers and alerts at least one crew member and at least one of the one or more passengers a priority position of the health status regarding the one or more passengers,
wherein the health monitoring system is further configured to generate a waiting list used for at least one of an analysis of the images or an alert to the crew member and the at least one of the one or more passengers by assigning priority positions of the one or more passengers in the waiting list based on at least one of an importance of the one or more passengers, a severity of health conditions, or a severity of contagiousness of health conditions.

11. The health monitoring system of claim 10, wherein the health monitoring system is configured such that: (1) the images are analyzed locally by a telemedical device to determine health data; and (2) the telemedical device transmits the health data to the telemedical monitoring system; and (3) a portable telemedical device transmits one or more of (i) the images and (ii) health data determined by analyzing the images, to a remote telemedical monitoring system via the communication network using the communication module; and (3) the portable telemedical device receives from the telemedical monitoring system via the communication network medical information regarding the passenger based on an analysis by the telemedical monitoring system of the one or more of (i) the images and (ii) the health data.

12. The health monitoring system of claim 11, further comprising an onboard management system, and wherein the health monitoring system is configured such that the telemedical device communicates with the telemedical monitoring system via the onboard management system.

13. The health monitoring system of claim 10, wherein a telemedical device transmits the images to the telemedical monitoring system, and the telemedical device receives from the telemedical monitoring system, via the communication network, medical information regarding the passenger based on an analysis of the images by the telemedical system to determine health data and an analysis of the health data by the telemedical system to determine medical information.

14. The health monitoring system of claim 10, further comprising an onboard management system, and wherein the health monitoring system is configured such that a telemedical device transmits the images to the onboard management system, and the onboard management system analyzes the images to determine health data, the health data is transmitted to the health monitoring system, and the telemedical device receives from the telemedical monitoring system via the communication network medical information regarding the passenger based on an analysis of the health data by the telemedical system to determine medical information.

15. A method of monitoring a health status of one or more passengers on a passenger vehicle, the method comprising:
an imaging device capturing images of a passenger on the vehicle;
analyzing the images and determining health data based on the images using a health monitoring application;
transmitting one or more of (i) the images and (ii) the health data determined by analyzing the images, to a remote telemedical monitoring system via a communication network; and
receiving from the telemedical monitoring system medical information regarding the passenger based on an analysis by the telemedical monitoring system of the one or more of (a) the images and (b) the health data,
wherein the analyzing further includes alerting a crew member and at least one of the one or more passengers of an action to take to manage the health status and generating a waiting list used for at least one of an analysis of the images or an alert to the crew member and the at least one of the one or more passengers by assigning priority positions of the one or more passengers in the waiting list based on at least one of an importance of the one or more passengers, a severity of health conditions, or a severity of contagiousness of health conditions.

16. The method of claim 15, wherein the one or more of (i) the images and (ii) the health data determined by analyzing the images, are transmitted to the telemedical monitoring system by an onboard management system, and the medical information is received from the telemedical monitoring system by the onboard management system.

17. The method of claim 16, wherein the onboard management system analyzes the images to determine the health data using a health monitoring application.

18. The method of claim 15, wherein the onboard management system transmits the images to the telemedical monitoring system, and the telemedical monitoring system analyzes the images to determine health data using a health monitoring application.

19. The method of claim 15, wherein the one or more of (i) the images and (ii) the health data determined by analyzing the images, are transmitted to the telemedical monitoring system by a portable telemedical device, and the medical information is received from the telemedical monitoring system by the portable telemedical device.

20. The method of claim 19, wherein the telemedical device transmits the images to the telemedical monitoring system, and the telemedical monitoring system analyzes the images to determine health data using a health monitoring application.

* * * * *